United States Patent
Nagao

(10) Patent No.: US 9,649,060 B2
(45) Date of Patent: May 16, 2017

(54) PUNCTURE NEEDLE CARTRIDGE AND PUNCTURE DEVICE USING SAME

(71) Applicant: Panasonic Healthcare Holdings Co., Ltd., Tokyo (JP)

(72) Inventor: Akio Nagao, Kagawa (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 101 days.

(21) Appl. No.: 14/406,634

(22) PCT Filed: Jul. 3, 2013

(86) PCT No.: PCT/JP2013/004137
§ 371 (c)(1),
(2) Date: Dec. 9, 2014

(87) PCT Pub. No.: WO2014/020826
PCT Pub. Date: Feb. 6, 2014

(65) Prior Publication Data
US 2015/0190082 A1  Jul. 9, 2015

(30) Foreign Application Priority Data
Jul. 31, 2012  (JP) ................................ 2012-169137

(51) Int. Cl.
*A61B 17/14* (2006.01)
*A61B 17/32* (2006.01)
(Continued)

(52) U.S. Cl.
CPC ...... *A61B 5/150633* (2013.01); *A61B 5/1513* (2013.01); *A61B 5/1519* (2013.01);
(Continued)

(58) Field of Classification Search
CPC ............ A61B 5/1411; A61B 5/150022; A61B 5/150412; A61B 5/15113; A61B 5/15117;
(Continued)

(56) References Cited

U.S. PATENT DOCUMENTS

2005/0149090 A1* 7/2005 Morita ................. A61B 5/1411
606/181
2005/0277850 A1* 12/2005 Mace .................... A61B 5/1411
600/584
(Continued)

FOREIGN PATENT DOCUMENTS

JP  2004-113580  4/2004
JP  2011-530317  12/2011
(Continued)

OTHER PUBLICATIONS

International Search Report issued Sep. 24, 2013 in International (PCT) Application No. PCT/JP2013/004137.

*Primary Examiner* — Katherine M Shi
(74) *Attorney, Agent, or Firm* — Wenderoth, Lind & Ponack, L.L.P.

(57) ABSTRACT

A puncture needle cartridge (1) includes: a lancet body (5) mounted with a puncture needle (3) on a front end side and having a mount (4) on a rear end side; and a plate-like first case (6) and second case (7) covering the lancet body (5) from above and below and arranged slidably back and forth along each other. The puncture needle cartridge (1) is configured such that the first case (6) is slid forward of the second case (7), and in this slid state, the first case (6) and the second case (7) are secured to each other when ejected from the puncture instrument (10). This can make the puncture needle cartridge (1) impossible to mount again on the puncture instrument (10).

9 Claims, 23 Drawing Sheets

(51) Int. Cl.
*A61B 5/15* (2006.01)
*A61B 5/151* (2006.01)

(52) U.S. Cl.
CPC .... *A61B 5/150022* (2013.01); *A61B 5/15111* (2013.01); *A61B 5/15113* (2013.01); *A61B 5/15117* (2013.01); *A61B 5/15194* (2013.01); *A61B 5/150412* (2013.01); *A61B 5/150549* (2013.01); *A61B 5/150618* (2013.01); *A61B 5/150648* (2013.01); *A61B 5/150717* (2013.01); *A61B 5/150916* (2013.01)

(58) Field of Classification Search
CPC ............ A61B 5/1513; A61B 5/150618; A61B 5/150717; A61B 5/1519; A61B 5/15194; A61B 5/150267; A61B 5/150549; A61B 5/150564; A61B 5/14532
USPC .................. 606/181, 182, 185; 600/583, 365
See application file for complete search history.

(56) References Cited

U.S. PATENT DOCUMENTS

| | | |
|---|---|---|
| 2009/0012427 A1 | 1/2009 | Fukuzawa |
| 2009/0198265 A1 | 8/2009 | Ono et al. |
| 2010/0036407 A1 | 2/2010 | Fowler et al. |
| 2011/0137203 A1* | 6/2011 | Nishiuchi ............ A61B 5/1411 600/583 |

FOREIGN PATENT DOCUMENTS

| | | |
|---|---|---|
| JP | 2012-120556 | 6/2012 |
| WO | 2006/046570 | 5/2006 |
| WO | 2006/118224 | 11/2006 |
| WO | 2010/015993 | 2/2010 |
| WO | 2012/046851 | 4/2012 |

* cited by examiner

PUNCTURE NEEDLE CARTRIDGE AND PUNCTURE DEVICE USING SAME

BACKGROUND OF THE INVENTION

1. Technical Field

The invention relates to a puncture needle cartridge for puncturing skin to allow the blood to be oozed in order to, for example, measure the blood sugar level, and to a puncture instrument using the cartridge.

2. Description of the Related Art

The configuration of such a puncture needle cartridge and a puncture instrument using it would conventionally be as follows.

That is, a puncture needle cartridge would comprise: a lancet body having a puncture needle on the front end side; a case covering the lancet body; and a protective cap covering the puncture needle (e.g. WO 2012/046851).

SUMMARY OF THE INVENTION

1. Problems to be Solved by the Invention

The conventional example would be configured to prevent reuse after puncture by securing the lancet body to a lock portion of the case. There would be some user-unfriendliness, however, since the puncture needle cartridge could be mounted again on the puncture instrument, which could mislead users into thinking that it could be reused.

A purpose of the invention is thus to improve user-friendliness by making the puncture needle cartridge impossible to mount again on the puncture instrument.

2. Means for Solving the Problems

In order to achieve this purpose, the invention is configured such that a puncture needle cartridge to be mounted on a puncture instrument comprises: a lancet body having a puncture needle on the front end side and having a mount on the rear end side; first and second cases covering the lancet body from above and below and arranged slidably along each other; a lock portion for securing the first and second cases to each other with one of the first and second cases being slid forward of the other; and a protective cap provided with an operation part on the front end side and inserted at the rear end side into the case to cover the puncture needle.

This allows the intended objective to be achieved.

3. Advantages of the Invention

As described above, the invention is configured such that a puncture needle cartridge to be mounted on a puncture instrument comprises: a lancet body having a puncture needle on the front end side and having a mount on the rear end side; first and second cases covering the lancet body from above and below and arranged slidably along each other; a lock portion for securing the first and second cases to each other with one of the first and second cases being slid forward of the other; and a protective cap provided with an operation part on the front end side and inserted at the rear end side into the case to cover the puncture needle. Accordingly, the puncture needle cartridge cannot be mounted again on the puncture instrument after use, which can improve user-friendliness as a result.

That is, in the present invention, even if an attempt to mount the protective cap on the puncture needle after use is made, the lancet body cannot be pressed backward with this protective cap. This prevents the puncture needle cartridge from being mounted again on the puncture instrument, and therefore can improve user-friendliness.

Moreover, since the cases are secured to each other with the first case being slid forward of the second case after use, it is obvious that the puncture needle cartridge has been used. The user will therefore not mistake it to be unused and will not try to use it again.

DETAILED DESCRIPTION OF EMBODIMENTS OF THE INVENTION

An embodiment of the invention will be described below with reference to the accompanying drawings.

Embodiment 1

Figure 1:
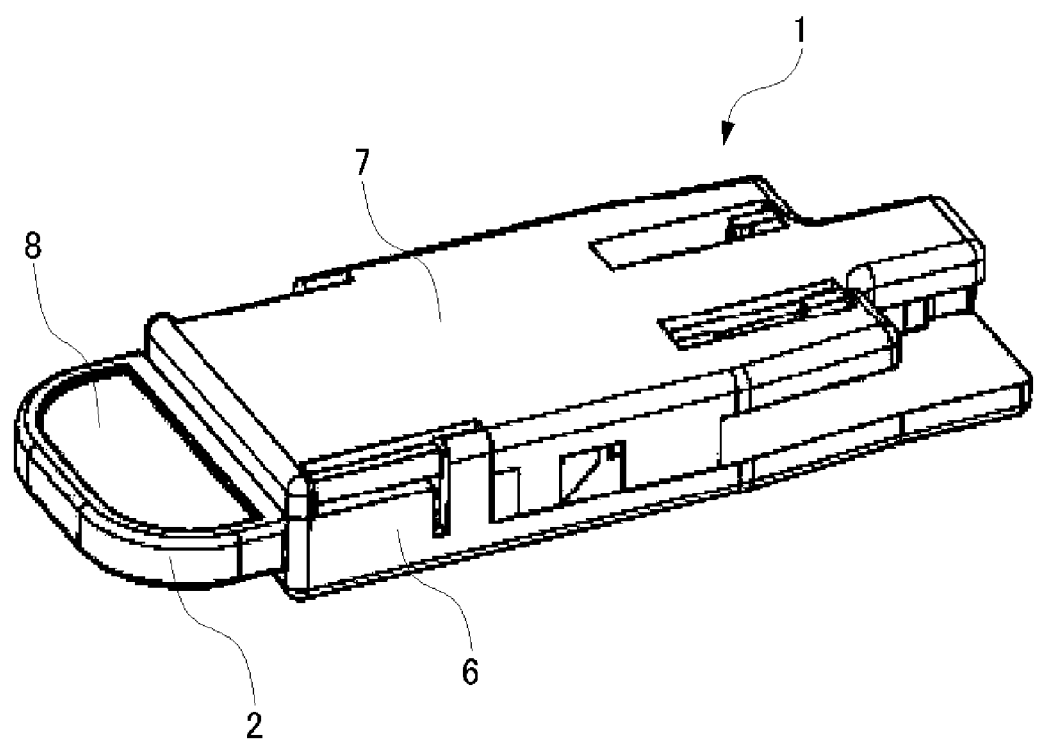
FIG. 1 is a general perspective view of a puncture needle cartridge according to one embodiment of the invention.

FIG. 1 shows a puncture needle cartridge 1. The puncture needle cartridge 1 is provided with a protective cap 2 on the front end side.

As shown in FIGS. 2 to 6, the puncture needle cartridge 1 comprises: a long rod-shaped lancet body 5; a long plate-like (not only long plate-like, but also long cylindrical etc.) first case 6 and second case 7 covering the lancet body 5 from above and below; and a protective cap 2. The lancet body 5 is mounted with a puncture needle 3 on the front end side, and has a mount 4 for a puncture instrument on the rear end side. The first case 6 and the second case 7 are arranged slidably back and forth along each other.

The protective cap 2 has an operation part 8 on the front end side to be operated with fingers. The protective cap 2 is inserted at the rear end side into a case formed with the first case 6 and second case 7 through an opening 9 provided on the front end side of the first case 6 and second case 7. The protective cap 2 is configured to cover the puncture needle 3 at the rear end side.

The first case 6 and the second case 7 are configured such that the first case 6 is slid forward of the second case 7 and in this completely-slid state the first case 6 and the second case 7 are secured to each other when ejected from the puncture instrument 10.

Figure 2:
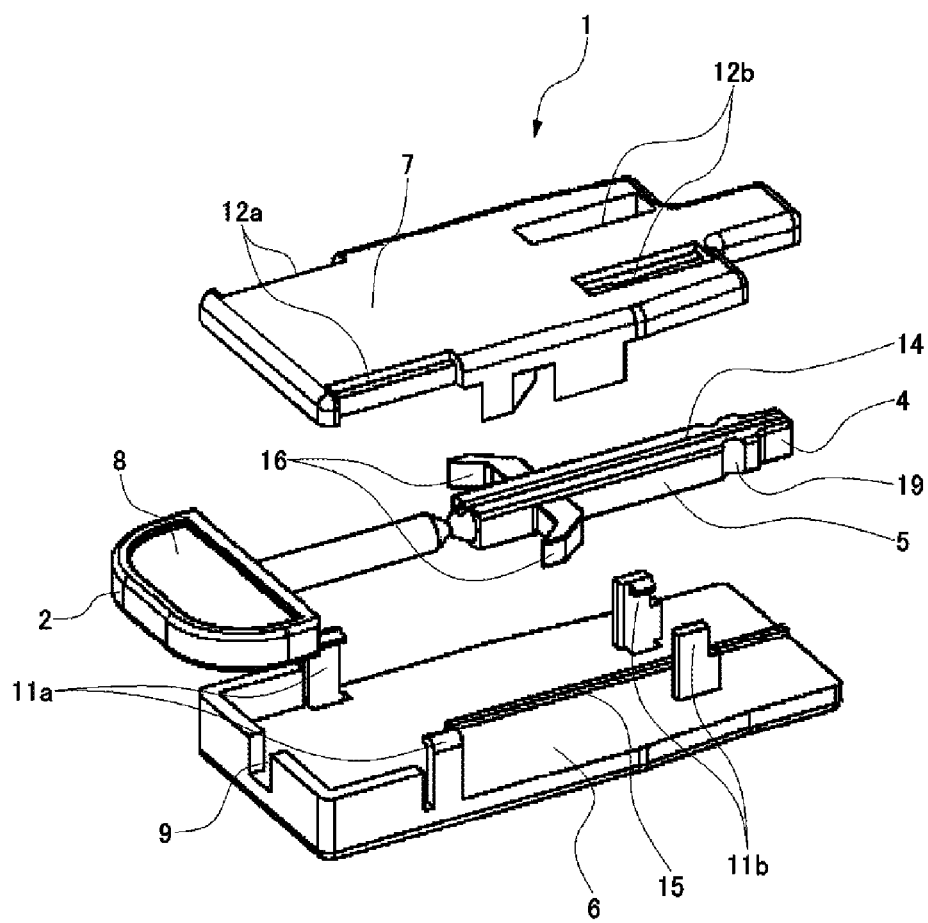
FIG. 2 is an exploded perspective view of the puncture needle cartridge according to the embodiment of the invention.

As shown in FIG. 2, the first case 6 has engagement portions 11a and 11b for the second case 7. The second case 7, at locations corresponding to the engagement portions 11a and 11b, has slide portions 12a and 12b (e.g. slide slots) along which these engagement portions 11a and 11b slide. On the front side of the slide portions (hereinafter referred to as the "slide end side") are provided lock portions 13 for locking the engagement portions 11b.

Describing in further detail, as shown in FIGS. 1 and 2, the first case 6 has first engagement portions 11a on both sides of the front end side, and has second engagement portions 11b in the inner regions on the rear end side. The tip portions of the first and second engagement portions 11a and 11b each bend inward in the first case 6 (medially in the first case 6) and are shaped such that the first and second engagement portions 11a and 11b can slide in first and second slide portions 12a and 12b, respectively.

The second case 7, on both sides of the front end side, has the first slide portions 12a along which the first engagement portions 11a slide and, in the inner regions on the rear end side, has the second slide portions 12b (slide slots) which the second engagement portions 11b come through and slide along. They are configured such that the tip portions of the first engagement portions 11a can slide in the slots of the first slide portions 12a and the tip portions of the second engagement portions 11b can slide in the slots of the second slide portions 12b.

Figure 3:
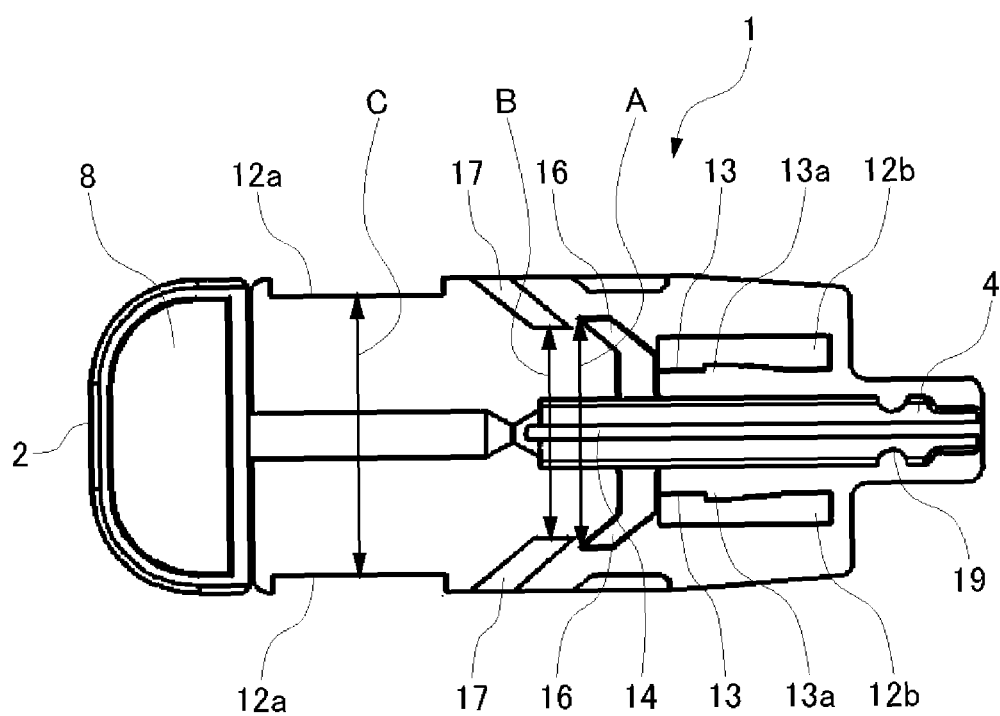
FIG. 3 is a top view of the puncture needle cartridge according to the embodiment of the invention.

The lock portions 13 will be described in detail. As shown in FIG. 3, the second slide portions 12b are shaped such that they gradually broaden outward as they go from the beginning of the slide (the rear side of the slide portions 12b) toward the end (the front side of the slide portions 12b). When the second engagement portions 11b slide toward the end, they slide moving gradually outward.

The second slide portions 12b are recessed inward near the end of the slide portions 12b.

That is, as shown in FIG. 3, bumps 13a (difference in level) are formed near the end of the slide portions 12b, and the tip portions of the second engagement portions 11b get over the bumps.

As a result, the lock portions 13 are formed with the end of the second slide portions 12b and the bumps 13a. These lock portions 13 locking the second engagement portions 11b limit the back-and-forth slide between the first case 6 and the second case 7.

As shown in FIG. 2, cuts 14 are provided on the top and bottom of the central part of the lancet body 5 from the front end to the rear end. Supporting portions 15 are provided inside the first and second cases 6 and 7 in locations corresponding to the cuts 14 (the supporting portion of the second case 7 is not shown).

The above-described engagement relation between the engagement portions 11a and 11b and the slide portions 12a and 12b as well as the engagement between the cuts 14 and the supporting portions 15 can further improve the stability of the lancet body 5 and the straight-going stability of the lancet body 5 during and after puncture.

Arm portions 16 provided on the lancet body 5 and protrusions 17 provided on the second case 17 for preventing re-puncture will be described below.

Figure 4:
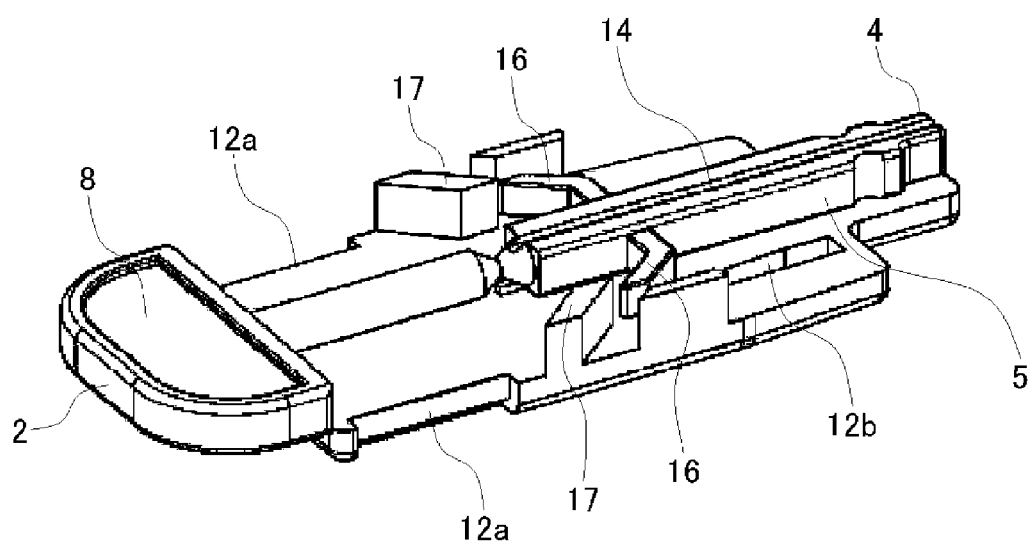
FIG. 4 is a perspective view of the puncture needle cartridge according to the embodiment of the invention.

As shown in FIGS. 3 and 4, the lancet body 5 has arm portions 16. The arm portions 16 extend between the puncture needle 3 and mount 4 of the lancet body 5 in a direction perpendicular to the lancet body 5.

As shown in FIG. 3, the arm portions 16 extend in a direction perpendicular to the lancet body 5 and, from the middle to the tip of the arm portions 16, slant in a tapered form toward the puncture direction.

The second case 7 has protrusions 17 to be engaged with the arm portions 16. The protrusions 17 are arranged between the first slide portions 12a and the second slide portions 12b and are shaped to protrude from the front end side of the puncture needle cartridge 1 toward the rear end side such that they engage with the tip portions of the arm portions 16.

As shown in FIG. 3, when the puncture needle cartridge 1 is not yet mounted on the puncture instrument 10, a width A between the tips of one of the arm portions 16 and the other is wider than a width B between the tips of the protrusions 17 provided on both sides inside the puncture needle cartridge 1, and is narrower than a width C between one of the first slide portions 12a and the other. This configuration prevents the arm portions 16 from being locked by the first case 6 and second case 7 and allows for a smooth puncture during puncture operation.

An operation performed from the mounting of the puncture needle cartridge 1 on the puncture instrument 10 to the ejection will be described next with reference to FIGS. 5 to 21.

Figure 5:
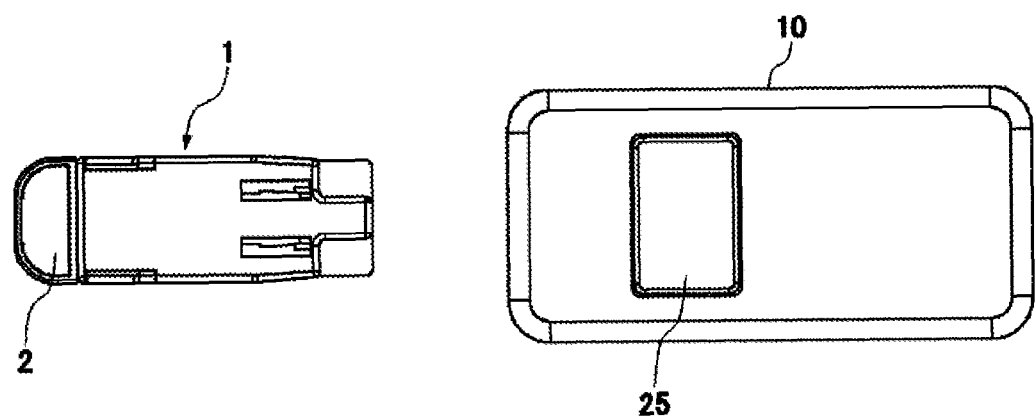
FIG. 5 is a top view of the puncture needle cartridge according to the embodiment of the invention in a state where it is mounted on a puncture instrument.
Figure 6:
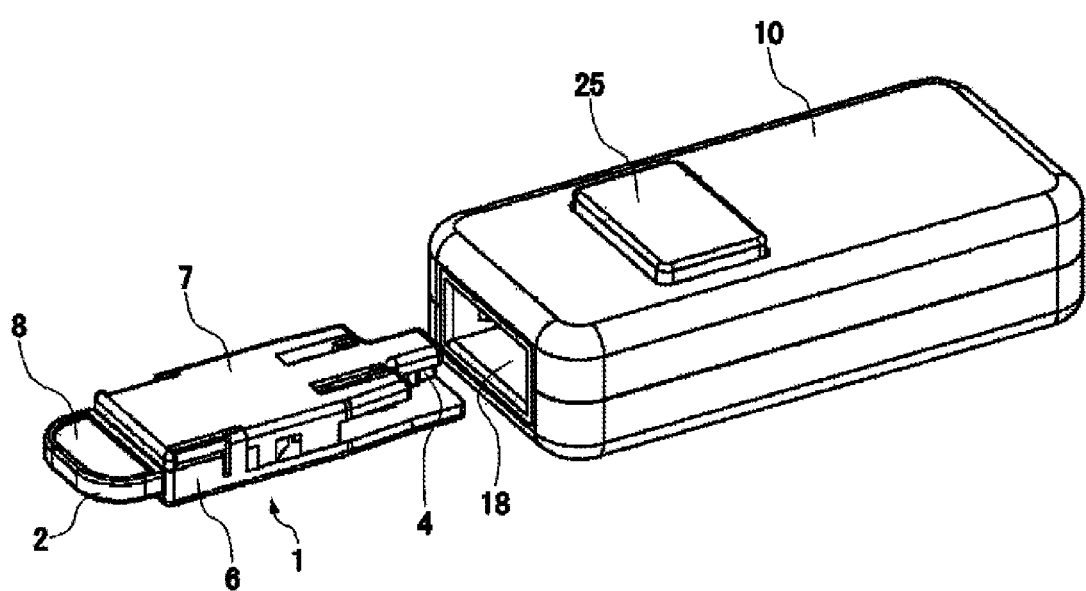
FIG. 6 is a perspective view of the puncture needle cartridge according to the embodiment of the invention in a state where it is mounted on the puncture instrument.
Figure 7:
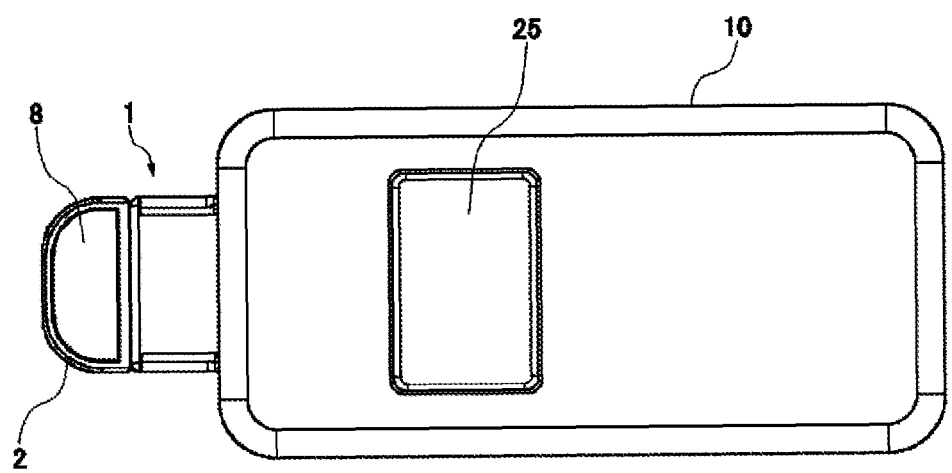
FIG. 7 is a top view of the puncture needle cartridge according to the embodiment of the invention in a state where it is mounted on the puncture instrument.
Figure 8:
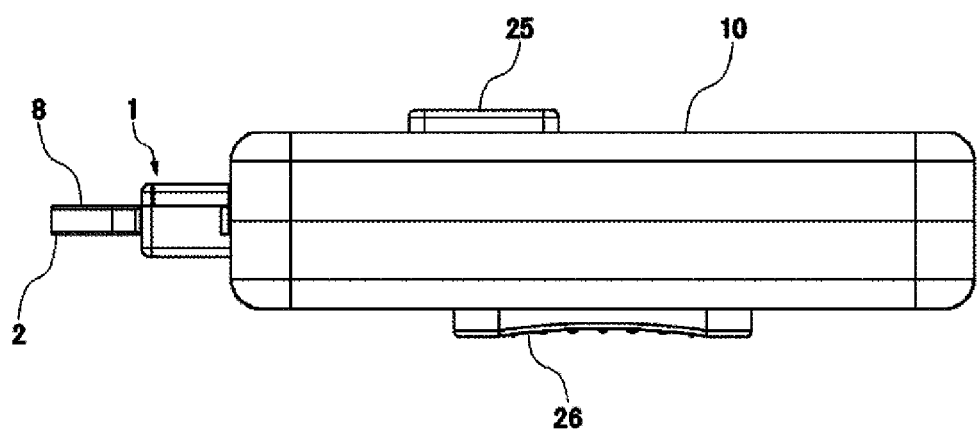
FIG. 8 is a side view of the puncture needle cartridge according to the embodiment of the invention in a state where it is mounted on the puncture instrument.
Figure 9:
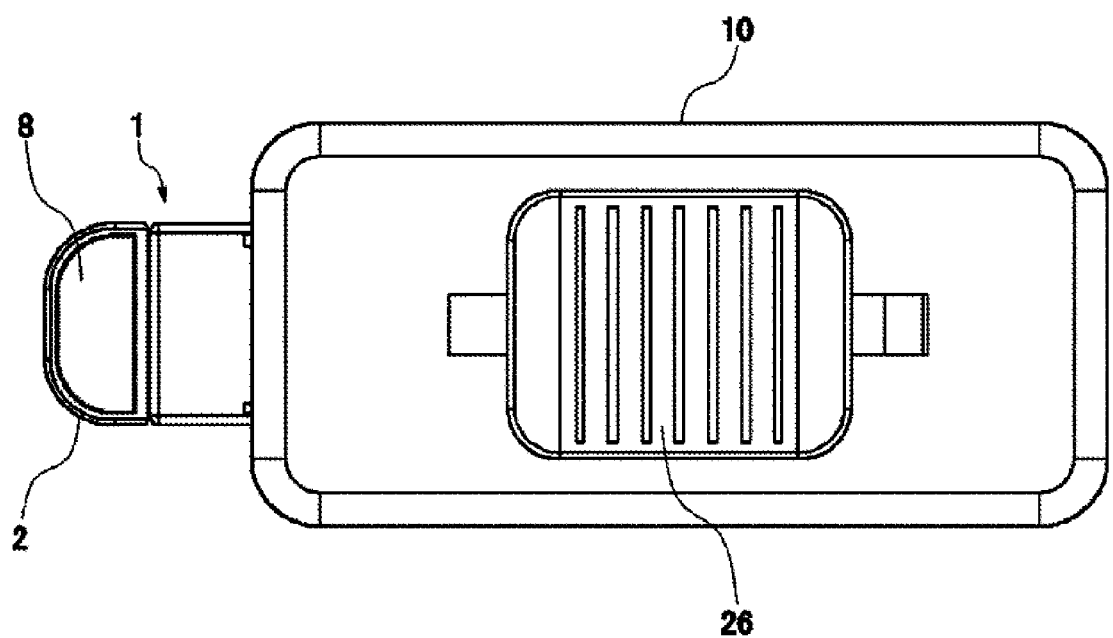
FIG. 9 is a rear view of the puncture needle cartridge according to the embodiment of the invention in a state where it is mounted on the puncture instrument.

FIGS. 5 and 6 show the puncture needle cartridge 1 and puncture instrument 10 before mounting.

The puncture needle cartridge 1 is mounted backward into a mount opening 18 of the puncture instrument 10. In this regard, though the shape of the first case 6 is different from that of the second case 7, the puncture needle cartridge 1 can be mounted with either side up as long as it is inserted backward into the mount opening 18.

FIGS. 7 to 13 show the puncture needle cartridge 1 mounted on the puncture instrument 10.

Figure 11:
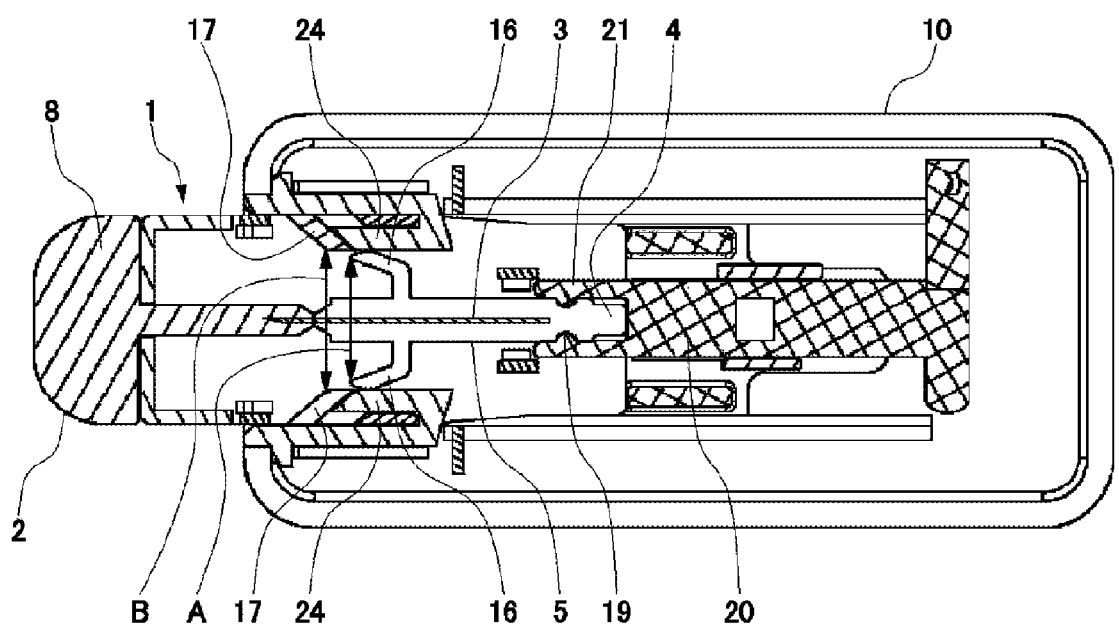
FIG. 11 is a cross-sectional top view of the puncture needle cartridge according to the embodiment of the invention in a state where it is mounted on the puncture instrument.

As shown in FIG. 11, on the rear end side of the lancet body 5 is the mount 4 (a groove 19 provided on the mount 4) to be mounted to the puncture instrument 10. The mount 4 is mounted to a gripping portion 21 on the front end side of a plunger 20 provided inside the puncture instrument 10.

When mounting, a user grips the operation part 8 and presses the puncture needle cartridge 1 in toward the rear end of the puncture instrument 10, resulting in the plunger 20 having the gripping portion 21 being pushed. This stretches a spring 23 (biasing object) provided via a coupling member 22 coupled to the rear end side of the plunger 20, accumulating biasing force against the lancet body 5 of the puncture needle cartridge 1.

As shown in FIG. 11, when the puncture needle cartridge 1 is mounted on the puncture instrument 10, contact members 24 provided inside the mount opening 18 of the puncture instrument 10 press the tip portions of the arm portions 16 from the rear end side. Accordingly, the tip portions of the arm portions 16 are elastically deformed inward (in a direction toward the shaft center of the lancet body 5).

As a result, the width A between the arm portions 16 becomes narrower than the width B between the protrusions 17, so that the arm portions 16 are not locked by the protrusions 17.

Figure 12:
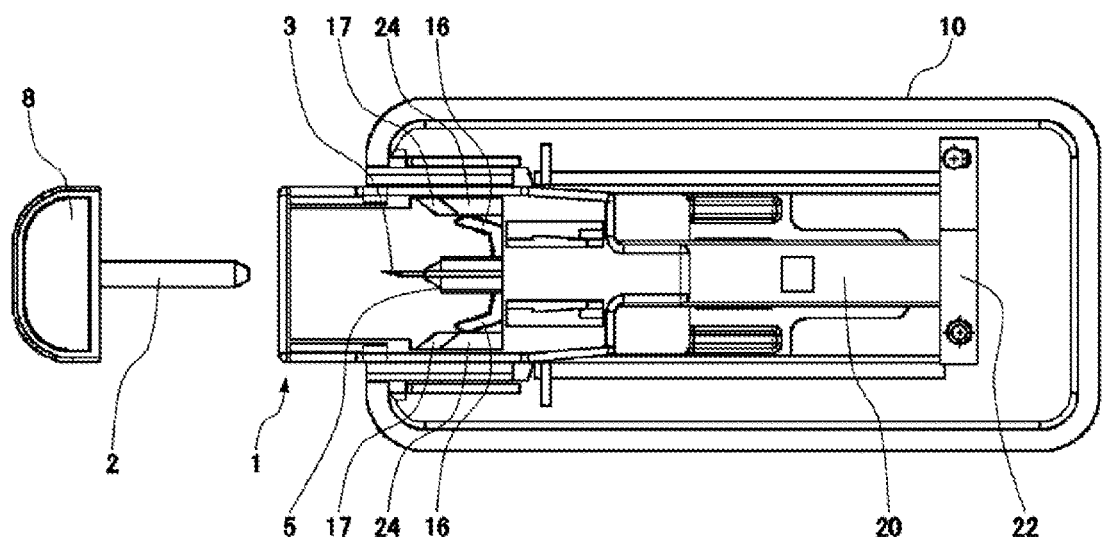
FIG. 12 shows a state where a protective cap is removed from the puncture needle cartridge according to the embodiment of the invention.

The protective cap 2 is then removed for puncture, as shown in FIG. 12. With the fingers gripping the operation part 8 provided on the front end side of the protective cap 2, the operation part 8 is rotated a certain angle to the left or right, so that the joint between the protective cap 2 and the lancet body 5 breaks and the protective cap 2 comes off the lancet body 5.

Figure 13:
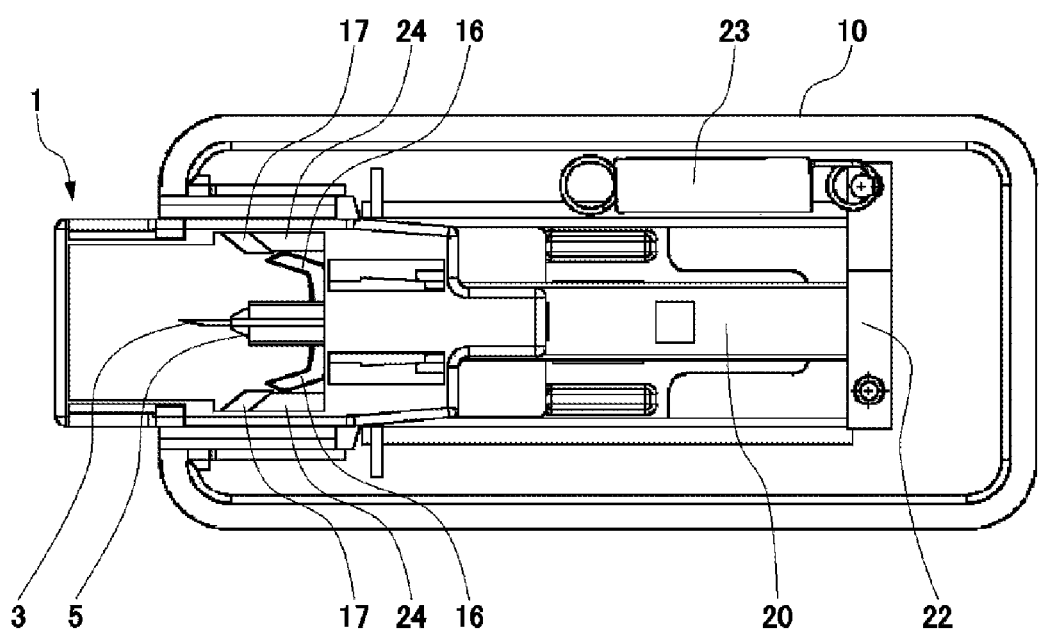
FIG. 13 shows an operation of the puncture needle cartridge according to the embodiment of the invention.

In this manner, as shown in FIG. 13, the puncture needle cartridge 1 gets into a puncture standby state (referred to as a first state).

The user then brings the skin (e.g. the left middle finger) into contact with the opening 9 of the puncture needle cartridge 1 (corresponding to a skin contact part) in order to puncture the skin to allow the blood to be oozed with the puncture instrument 10.

Figure 14:
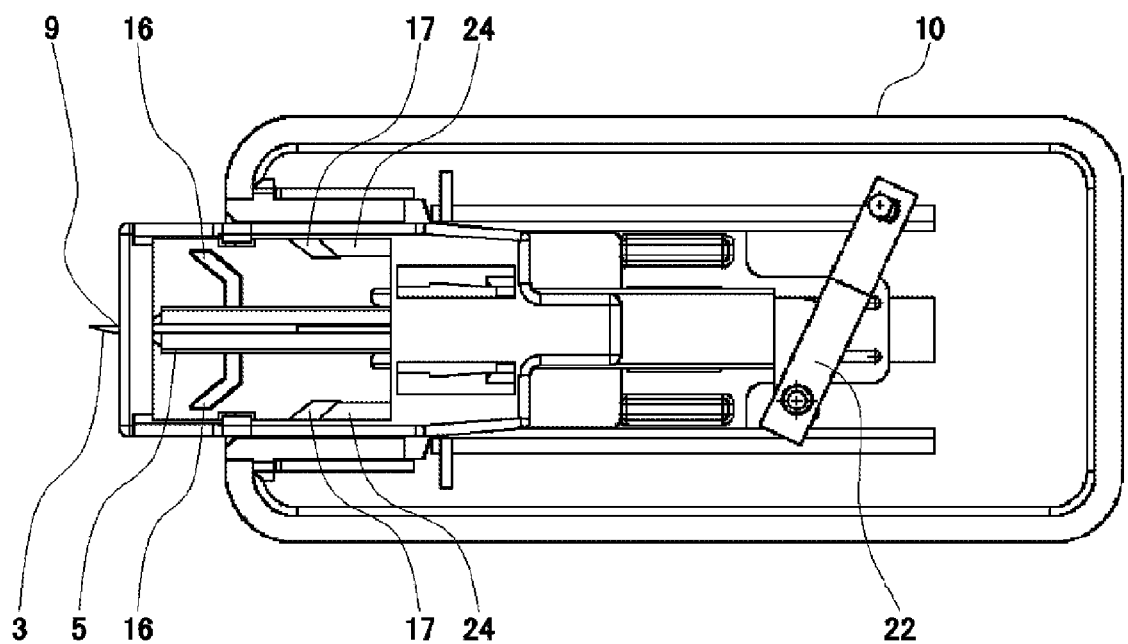
FIG. 14 shows an operation of the puncture needle cartridge according to the embodiment of the invention.

As shown in FIG. 14, a puncture operation button 25 provided on the side of the puncture instrument 10 is pushed with a finger (e.g. the right index finger) to release the biasing force accumulated in the spring 23, so that the plunger 20 coupled to the spring 23 quickly moves toward the front end. Accordingly, the lancet body 5 moves toward the front end. As previously described, since the width A between the arm portions 16 is smaller than the width B between the protrusions 17, the arm portions 16 go through the protrusions 17 and the lancet body 5 is not prevented from moving. As the lancet body 5 moves, the puncture needle 3 moves to the front end side, goes through the opening 9, and puncture the skin. This allows the blood to be oozed and collected (this is referred to as a second state).

Figure 15:
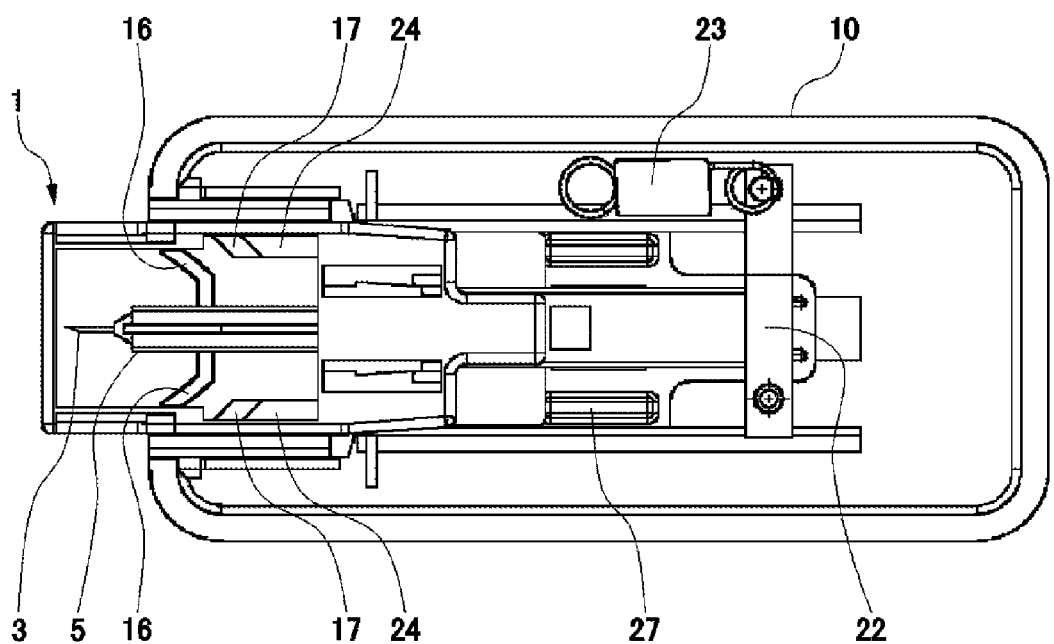
FIG. 15 shows an operation of the puncture needle cartridge according to the embodiment of the invention.
Figure 16:
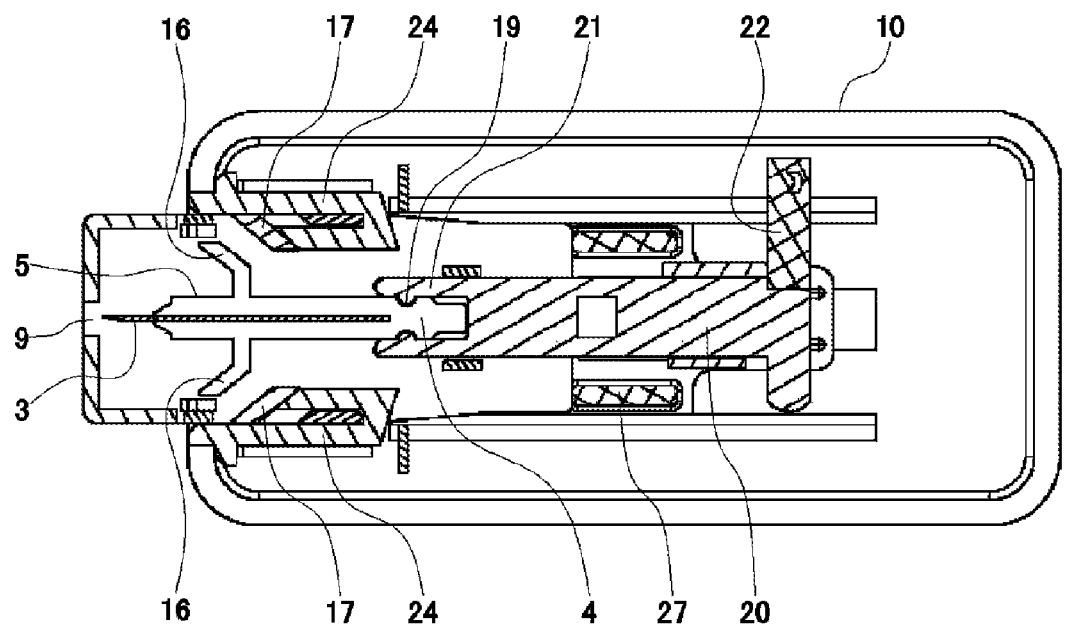
FIG. 16 shows an operation of the puncture needle cartridge according to the embodiment of the invention.

After the skin is punctured and as the spring 23 returns back, the puncture needle 3 (lancet body 5) returns toward the rear end and is located in the rear end side behind the opening 9, as shown in FIGS. 15 and 16 (this is referred to as a third state).

An operation to eject the puncture needle cartridge 1 after puncture from the puncture instrument 10 will next be described with reference to FIGS. 17 to 21.

An ejection lever 26 (see FIGS. 8 and 9) provided on the side of the puncture instrument 10 (the back of the puncture operation button 25) is operated in order to eject the puncture needle cartridge 1 after puncture. In this example, the ejection lever 26 is slid toward the front end of the puncture instrument 10.

Figure 17:
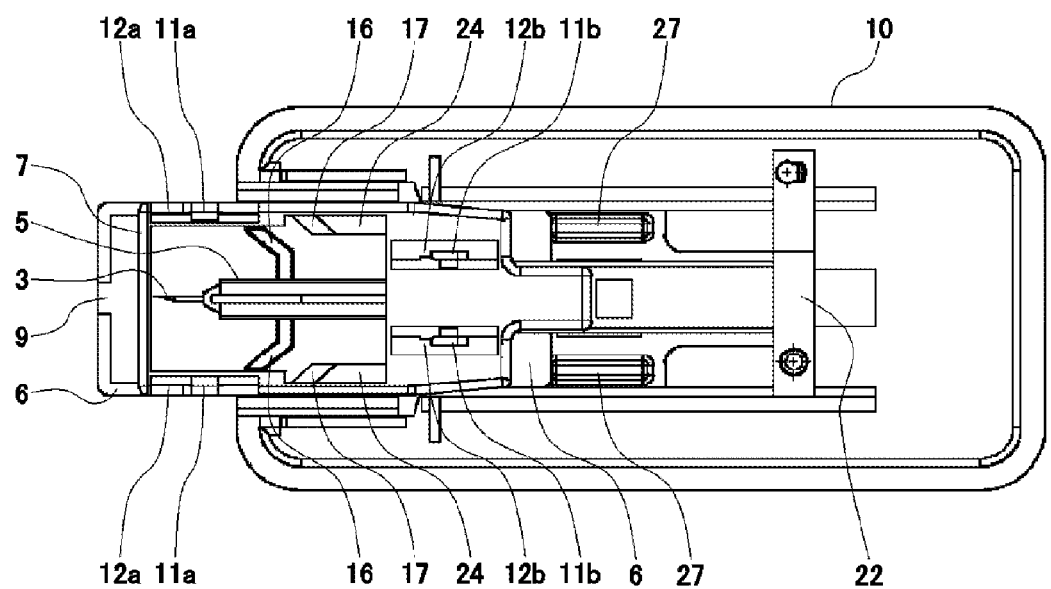
FIG. 17 shows an operation of the puncture needle cartridge according to the embodiment of the invention.

As shown in FIG. 17, an ejection member 27 coupled to the ejection lever 26 then slides toward the front end of the puncture instrument 10.

Figure 10:
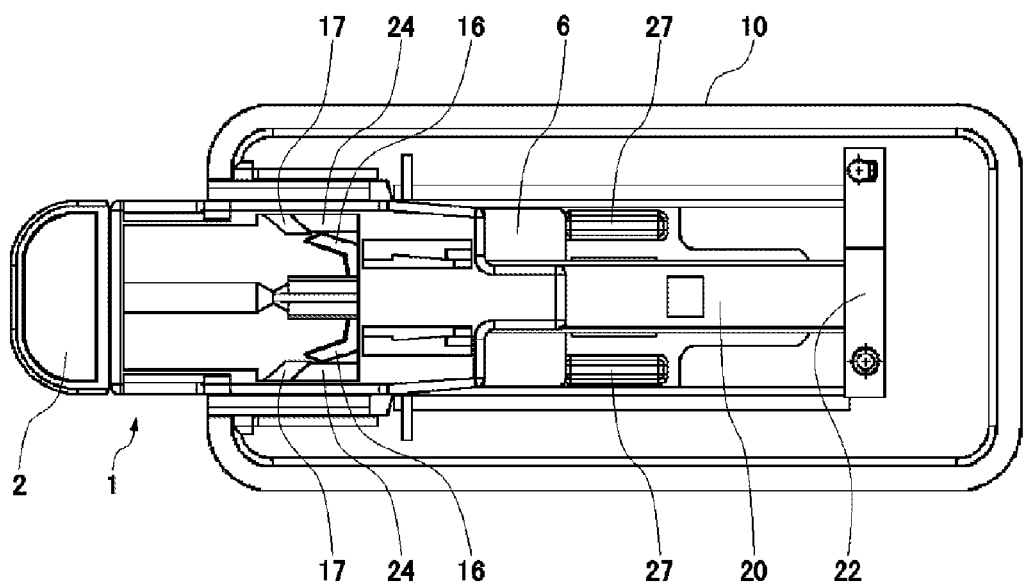
FIG. 10 is a cross-sectional top view of the puncture needle cartridge according to the embodiment of the invention in a state where it is mounted on the puncture instrument.

When the puncture needle cartridge 1 is mounted, the front end side of the ejection member 27 is in contact with the rear end side of the first case 6 (the state shown in FIG. 10). Consequently, the movement of the ejection member 27 toward the front end accordingly makes the first case 6 also move toward the front end of the puncture needle cartridge 1 as shown in FIGS. 17 and 18.

As the first case 6 moves toward the front end, the tip portions of the first engagement portions 11a and the tip portions of the second engagement portions 11b begin to slide in the slots of the first slide portions 12a and in the slots of the second slide portions 12b, respectively, toward the front end.

When the first case 6 is moved to the front end side by the ejection member 27, the first engagement portions 11a stop at the end side of the first slide portions 12a, and the tip portions of the second engagement portions 11b fit to the lock portions 13 provided on the end side of the second slide portions 12b. As a result, the first case 6 and the second case 7 are engaged with each other.

Figure 18:
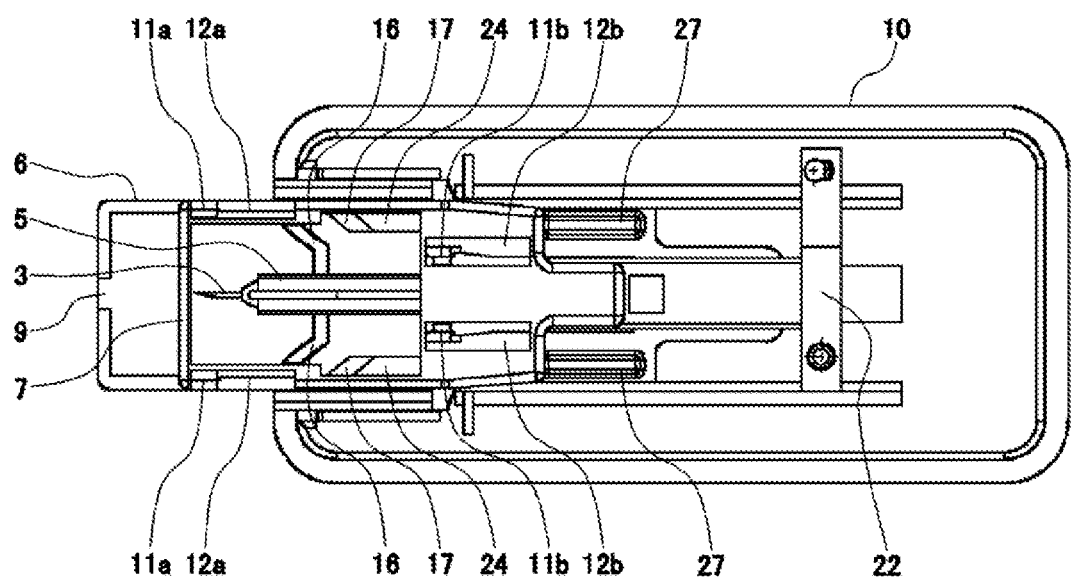
FIG. 18 shows the ejection of the puncture needle cartridge according to the embodiment of the invention.

That is, as shown in FIG. 18, the second engagement portions 11b fit to the recess-shaped lock portions 13 provided on the end side of the second slide portions 12b, whereby the first case 6 and the second case 7 are engaged with each other with the first case 6 being moved forward of the second case 7.

The rear end portion of the first case 6 and the rear end portion of the second case 7 then overlap each other.

The distance between the opening 9 and the puncture needle 3 thus becomes long as the first case 6 moves forward of the second case 7.

In this state, if the ejection member 27 is moved further toward the front end, the ejection member 27 pushes out the engaged first case 6 and second case 7 together. At the same time, the protrusions 17 move forward as the first case 6 and the second case 7 move forward.

At this point, the mount 4 of the lancet body 5 is still mounted to the gripping portion 21 of the puncture instrument 10. Therefore, the arm portions 16 of the lancet body 5 located in front of the protrusions 17 do not move forward, but the engaged first case 6 and second case 7 move forward.

Figure 19:
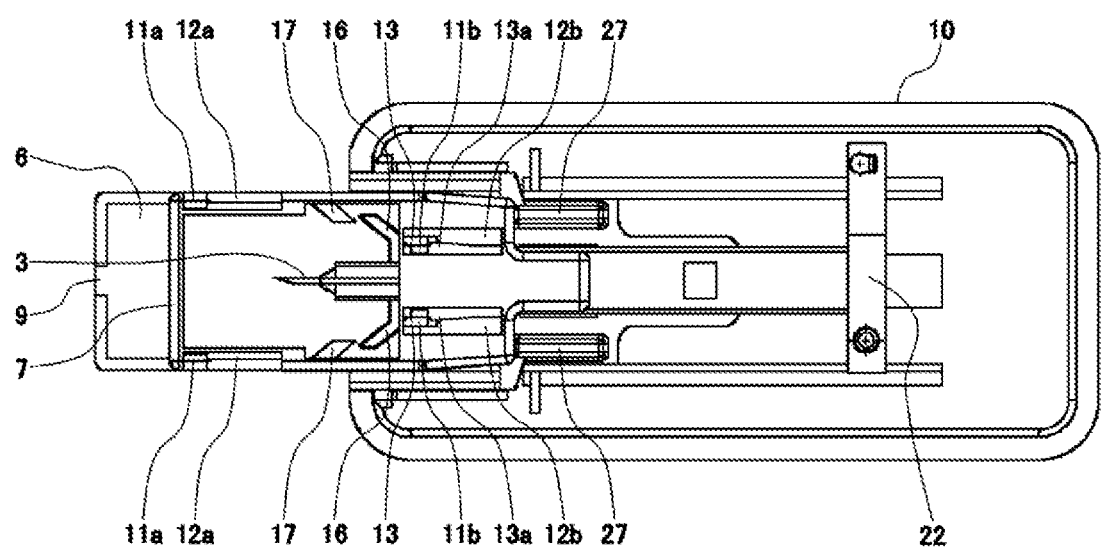
FIG. 19 shows the ejection of the puncture needle cartridge according to the embodiment of the invention.

As a result, as shown in FIG. 19, the tip portions of the arm portions 16 located in front of the protrusions 17, in such a way as to be pushed from the rear end side by the protrusions 17, elastically deform inward, go over the protrusions 17, and move to the rear end side behind the protrusions 17. After going over the protrusions 17, the elastically-deformed tip portions of the arm portions 16 go back to the original state, so that the protrusions 17 and the arm portions 16 are somewhat engaged with each other (a fourth state).

Figure 21:
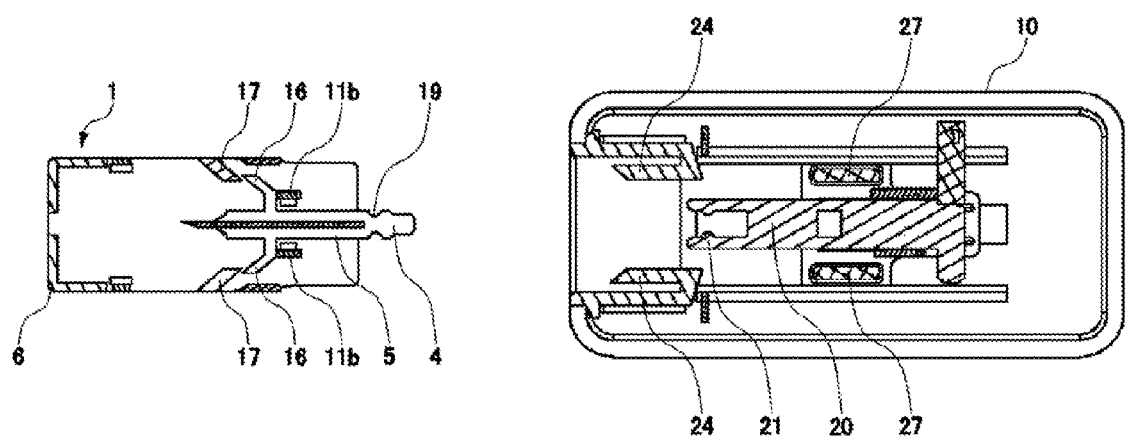
FIG. 21 shows the ejection of the puncture needle cartridge according to the embodiment of the invention.

Then, the orthogonal portions of the arm portions 16 are engaged with the front end portions of the second engagement portions 11b, as shown in FIG. 21.

Figure 20:
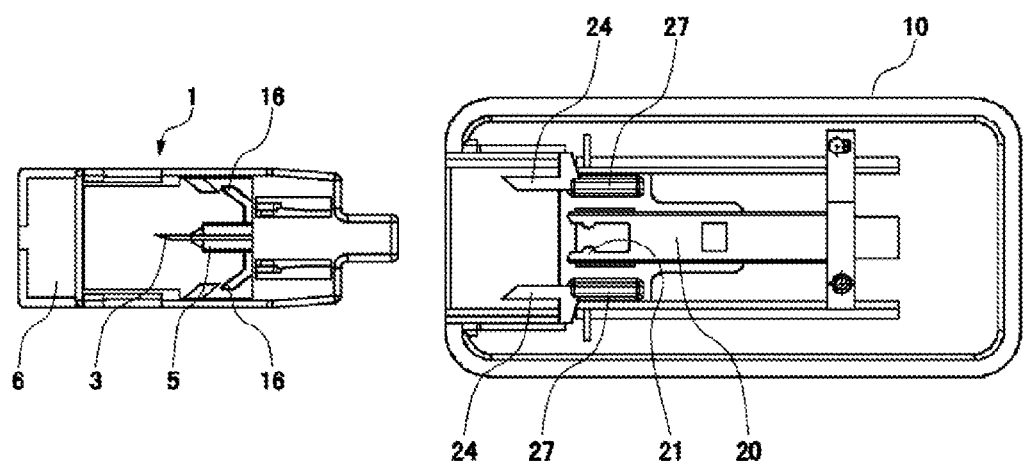
FIG. 20 shows the ejection of the puncture needle cartridge according to the embodiment of the invention.

As shown in FIGS. 20 and 21, the front end portions of the arm portions 16 of the lancet body 5 are engaged with the protrusions 17, and the rear end portions of the arm portions 16 are engaged with the front end portions of the second engagement portions 11b. If the ejection member 27 is moved further toward the front end in this state, the mount 4 (the groove 19) now becomes detached from the gripping portion 21 when the force to push the puncture needle cartridge 1 forward becomes larger than the force with which the mount 4 of the lancet body 5 is mounted to the gripping portion 21 of the puncture instrument 10, and the puncture needle cartridge 1 is ejected from the puncture instrument 10 (a fifth state).

After ejecting the puncture needle cartridge 1, the ejection member 27 returns to its original position, the rear end side of the puncture instrument 10.

Now, a situation where an attempt to mount the ejected puncture needle cartridge 1 again on the puncture instrument 10 after use is made will be described with reference to FIGS. 22 and 23.

Figure 22:
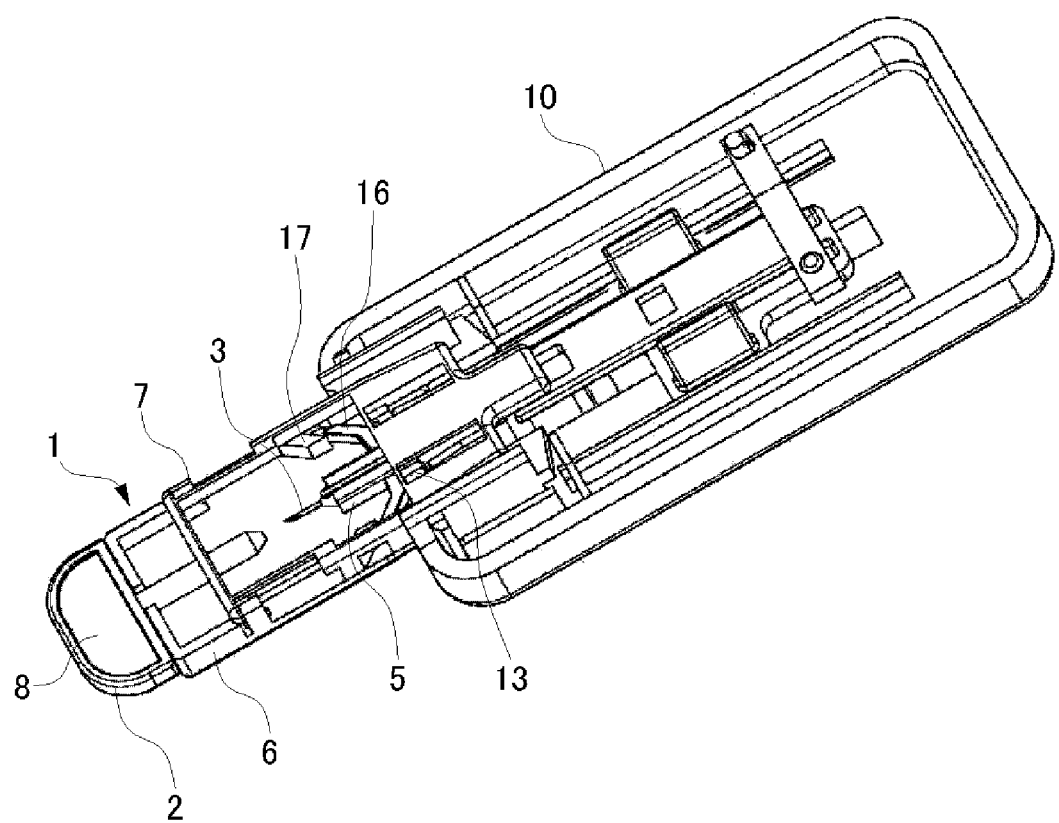
FIG. 22 shows an attempt to mount again the puncture needle cartridge according to the embodiment of the invention.
Figure 23:
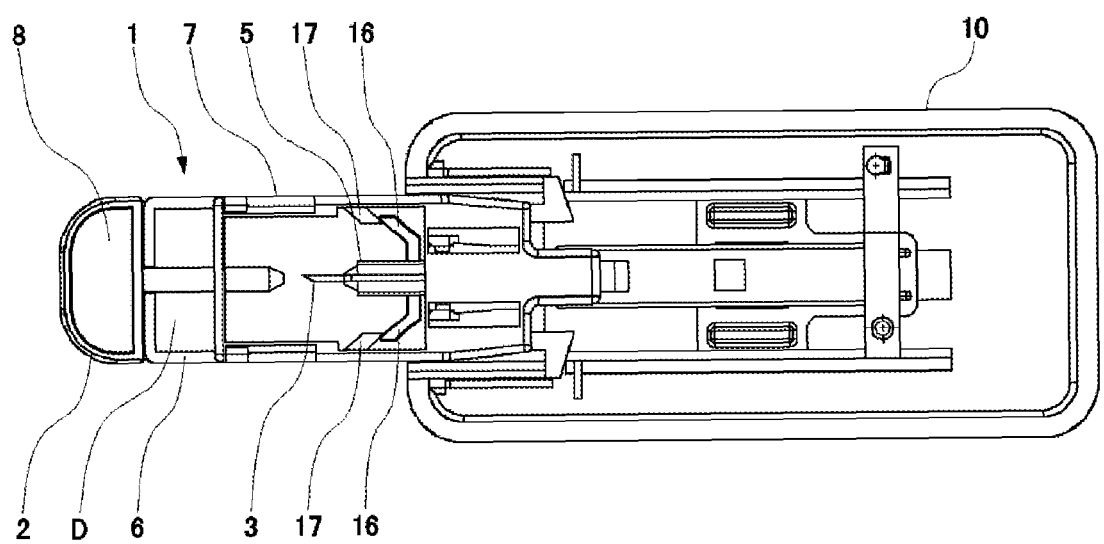
FIG. 23 shows the attempt to mount again the puncture needle cartridge according to the embodiment of the invention.

As shown in FIGS. 22 and 23 and as described above, in the ejected puncture needle cartridge 1, the first case 6 is located forward of the second case 7 and the second engagement portions 11b are inserted in the lock portions 13, so that the first case 6 and the second case 7 are secured to each other and, as a result, are engaged with each other.

The puncture needle cartridge 1 is in a state where the arm portions 16 are engaged with the protrusions 17 and the puncture needle 3 cannot move toward the front end.

Then, an attempt to attach the protective cap 2 again to the puncture needle cartridge 1 is made as shown in FIGS. 22 and 23. In this state, between the rear end portion of the protective cap 2 and the front end portion of the puncture needle 3 exists a gap corresponding to the distance for which the first case 6 has moved forward of the second case 7.

Accordingly, even if there is an attempt to mount the ejected puncture needle cartridge 1 again on the puncture instrument 10 with the operation part 8 of the protective cap 2 being gripped, the force to mount it again is not appropriately transmitted to the lancet body 5 due to the gap between the protective cap 2 and the puncture needle 3. As shown in FIG. 23, the force for the re-mounting is applied from the rear end side of the lancet body 5 and the arm portions 16 of the lancet body 5 become engaged with the protrusions 17, whereby the re-mounting is impossible.

This can make the puncture needle cartridge 1 impossible to mount again on the puncture instrument 10, thus preventing a user from reusing the puncture needle cartridge 1 and increasing safety.

The state where the first case 6 has moved forward of the second case 7 can make the cartridge recognized as already been used and as unable to reuse, accordingly preventing an operation attempting to reuse. From these viewpoints, user-friendliness is improved.

As a way to call attention to the reuse of the puncture needle cartridge 1 for the puncture instrument 10, a sign indicating that the cartridge is used may be provided in the space between the first case 6 and the second case 7 left by the first case 6 of the ejected puncture needle cartridge 1 having moved forward of the second case 7 (e.g. D in FIG. 23).

This can show more clearly that the puncture needle cartridge 1 is used and can call the attention of a user who tries to reuse mistakenly.

As stated above, the embodiment can make the puncture needle cartridge 1 impossible to reuse for the puncture instrument 10, thus increasing safety.

As stated above, the invention can prevent the reuse for the puncture instrument, thus increasing safety.

Accordingly, the invention is expected to be used, for example, as a puncture needle cartridge to be used for measuring the blood sugar level and as a puncture instrument using the cartridge.

DESCRIPTION OF THE SYMBOLS

1: Puncture needle cartridge
2: Protective cap
3: Puncture needle
4: Mount
5: Lancet body
6: First case
7: Second case
8: Operation part
9: Opening
10: Puncture instrument
11a: First engagement portion
11b: Second engagement portion
12a: First slide portion
12b: Second slide portion
13: Lock portion
13a: Bump
14: Cut
15: Supporting portion
16: Arm portion
17: Protrusion
18: Mount opening
19: Groove
20: Plunger
21: Gripping portion
22: Coupling member
23: Spring
24: Contact member
25: Puncture operation button
26: Ejection lever
27: Ejection member

The invention claimed is:

1. A puncture needle cartridge to be mounted on a puncture instrument, the puncture needle cartridge comprising:
   a lancet body having a puncture needle on a front end side and having a mount on a rear end side;
   a case including a first case and a second case, the first and second cases covering the lancet body from above and below, respectively, and the first and second cases are arranged slidably along each other;
   a lock portion for securing the first and second cases to each other with one of the first and second cases being slid axially forward of the other; and
   a protective cap provided with an operation part on a front end side of the case, the operation part being inserted into the case to cover the puncture needle.

2. The puncture needle cartridge according to claim 1, wherein the first and second cases are secured to each other with one of the first and second cases being slid forward of the other when ejected from the puncture instrument.

3. The puncture needle cartridge according to claim 1, wherein one of the first and second cases comprises an engagement portion, and the other of the first and second cases comprises:
   a slide portion along which the engagement portion slides; and
   the lock portion for locking the engagement portion with one of the first and second cases being slid forward of the other.

4. The puncture needle cartridge according to claim 3, wherein the lock portion is formed with a recess.

5. The puncture needle cartridge according to claim 3, wherein the first case comprises:
- a first engagement portion located on the front end side; and
- a second engagement portion located on the rear end side, and the second case comprises:
- a first slide portion, located on the front end side, along which the first engagement portion slides; and
- a second slide portion, located on the rear end side, along which the second engagement portion slides.

6. The puncture needle cartridge according to claim 5, wherein the first engagement portion is provided in the outer region on the front end side of the first case, the second engagement portion is provided in the inner region on the rear end side of the first case, and the second slide portion is formed with a slide slot passing through the second case.

7. The puncture needle cartridge according to claim 1, wherein the lancet body has an arm portion extending in a direction perpendicular to the lancet body, and the second case has a protrusion, in front of the arm portion, for engagement with the arm portion.

8. The puncture needle cartridge according to claim 7, having a configuration in which the first case slides forward of the second case toward the front end.

9. The puncture needle cartridge according to claim 1, wherein the first and second cases are plate-like objects.

* * * * *